(12) United States Patent
Sharma et al.

(10) Patent No.: US 7,470,810 B2
(45) Date of Patent: Dec. 30, 2008

(54) ALKYL AND ARYL-THIOTRIFLUOROACETATES AND PROCESS

(75) Inventors: Padam N. Sharma, Manlius, NY (US); Edward J. Gublo, Liverpool, NY (US); Susan D. Boettger, Fayetteville, NY (US); Saibaba Racha, Fayetteville, NY (US); John Usher, Dewitt, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 623 days.

(21) Appl. No.: 11/032,734

(22) Filed: Jan. 11, 2005

(65) Prior Publication Data

US 2005/0159612 A1    Jul. 21, 2005

Related U.S. Application Data

(60) Provisional application No. 60/537,832, filed on Jan. 21, 2004.

(51) Int. Cl.
  *C07C 321/04* (2006.01)
(52) U.S. Cl. ..................................... 562/431
(58) Field of Classification Search ................. 562/431
  See application file for complete search history.

(56) References Cited

U.S. PATENT DOCUMENTS 3,325,478 A * 6/1967 Hermann et al. ............ 540/331
6,395,767 B2   5/2002 Robl et al.

FOREIGN PATENT DOCUMENTS

WO    2005/073185    * 11/2005

OTHER PUBLICATIONS

U.S. Appl. No. 10/989,138, filed Nov. 15, 2004, Stephen O'Connor et al.

U.S. Appl. No. 60/574,177, filed May 25, 2004, Padam Sharma.
U.S. Appl. No. 60/600,510, filed Aug. 11, 2004, Padam Sharma et al.
U.S. Appl. No. 10/716,012, filed Nov. 18, 2003, Truc Vu et al.

* cited by examiner

*Primary Examiner*—James O. Wilson
*Assistant Examiner*—Ebenezer Sackey
(74) *Attorney, Agent, or Firm*—Burton Rodney

(57) ABSTRACT

Novel $C_3$-$C_{19}$ alkyl- and aryl-thiotrifluoroacetates are provided which have the structure

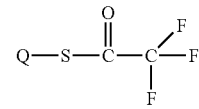

wherein Q is $C_9$-$C_{19}$ alkyl or aryl, and are useful protecting agents for the amino or hydroxy functional groups of amines, amino acids or primary or secondary alcohols or amino alcohols to enable formation of amide bonds in peptides or proteins which are useful as screening agents, pharmaceuticals and cosmetics.

A process for preparing $C_3$-$C_{19}$ alkyl- and aryl-thiotrifluoroacetates is also provided wherein a $C_3$-$C_{19}$ alkylthiol or arylthiol is treated with trifluoroacetic anhydride (TFAA) in the presence of organic base such as pyridine, a solvent such as dichloromethane (DCM) and dimethylaminopyridine (DMAP) as a catalyst to form the desired $C_3$-$C_{19}$ alkyl- or aryl-thiotrifluoroacetate.

In addition, a process for protecting a primary or secondary amino group or a primary or secondary hydroxyl group or an amino alcohol with a trifluoroacetyl protecting group is provided wherein a primary or secondary amine, amino acid, a primary or secondary alcohol or an amino alcohol is treated with a $C_3$ to $C_{19}$ alkyl- or aryl-thiotrifluoroacetate in basic aqueous solution.

8 Claims, No Drawings

ALKYL AND ARYL-THIOTRIFLUOROACETATES AND PROCESS

FIELD OF THE INVENTION

This application claims a benefit of priority from U.S. Provisional Application No. 60/537,832, filed Jan. 21, 2004, the entire disclosure of which is herein incorporated by reference.

The present invention relates to novel $C_9$-$C_{19}$ alkyl- and aryl-thiotrifluoroacetates which are useful as protecting agents for primary or secondary amino groups or hydroxyl groups such as in amino acids, amino alcohols or primary or secondary alcohols, and to a process for preparing the $C_3$-$C_{19}$ alkyl- and aryl-thiotrifluoroacetates.

BACKGROUND OF THE INVENTION

Protection of the amino functional groups of amino acids is essential for the formation of amide bonds. Amino acids are generally water soluble and basic conditions are required for their protection. The commonly issued protecting (acylating) reagents such as trifluoroacetic anhydride (TFAA), $C_2H_5OCOCF_3$, $CH_3OCOCF_3$, (trifluoroacetyl) benzotriazole, bismuth (III) triflate ($Bi(OTF_3)$) and pyridinium trifluoroacetate (TFAP) have been found to be unstable in basic aqueous medium. Ethyl thiotrifluoroacetate has been used as a protecting agent for amino acids in aqueous basic media. However, the ethanethiol by-product formed during the protection reaction has a particularly unpleasant, intolerable odor and thus cannot be used in manufacturing processes.

Accordingly, a need exists for an acylating agent such as a trifluoro-acylating agent which is non-odorous and stable in aqueous basic medium.

BRIEF DESCRIPTION OF THE INVENTION

In accordance with the present invention, novel $C_9$-$C_{19}$ alkyl- and aryl-thiotrifluoroacetate protecting agents are provided which are substantially non-odorous, and whose by-products are non-odorous and stable in aqueous basic medium. The $C_9$-$C_{19}$ alkyl- and aryl-thiotrifluoroacetates of the invention have the structure

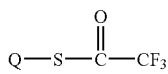

I where Q is a $C_9$-$C_{19}$ alkyl group which may be straight chained or branched, or aryl.

In addition, in accordance with the present invention, a process is provided for preparing a $C_3$-$C_{19}$ alkyl- and aryl-thiotrifluoroacetates of formula IA of the invention

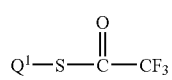

IA where $Q^1$ is $C_3$ to $C_{19}$ alkyl or aryl, which includes the step of reacting a $C_3$-$C_{19}$ alkylthiol or an arylthiol with a trifluoroacylating agent which preferably is trifluoroacetic anhydride (TFAA), in the presence of an organic base such as pyridine, a solvent such as dichloromethane (DCM) and a catalyst such as 4-dimethylamino pyridine (DMAP).

In addition, in accordance with the present invention, a process is provided for protecting primary or secondary amino groups or primary or secondary hydroxyl groups or amino alcohols with a trifluoroacetyl protecting group in an aqueous solvent, which includes the step of treating a primary or secondary amine or amino acid, or a primary or secondary alcohol or an amino alcohol with a basic aqueous solution of a $C_3$ to $C_{19}$ alkyl- or aryl-thiotrifluoroacetate, to cause the amino group or hydroxyl group to be protected as its trifluoroacetamide.

In a preferred embodiment, the $C_3$-$C_{19}$ alkylthiol will be 1-dodecanethiol, and the $C_3$-$C_{19}$ alkyl thiotrifluoroacetates produced will be 1-dodecane-thiotrifluoroacetate ($CH_3(CH_2)_{11}SCOCF_3$). 1-Dodecanethiotrifluoroacetate is particularly useful in converting amine II to amide III

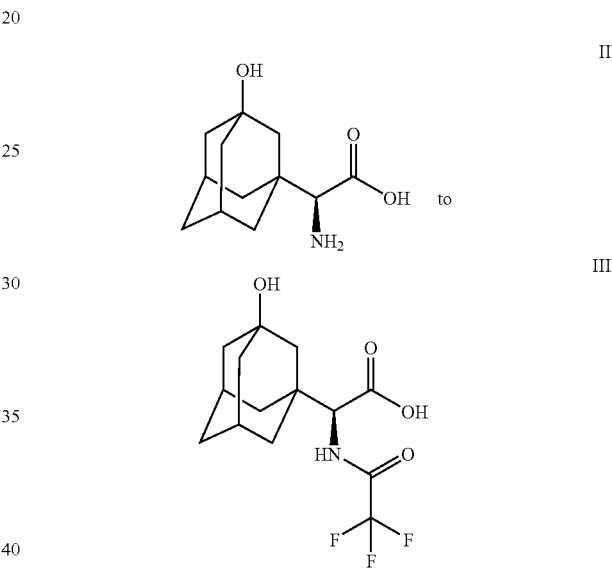

which is useful in preparing anti-diabetic agents and anti-obesity agents as disclosed in U.S. Pat. No. 6,395,767.

Compound II may be prepared as described in U.S. Pat. No. 6,395,767 and U.S. application Ser. No. 10/716,012 based on provisional application No. 60/431,814 filed Dec. 9, 2002.

DETAILED DESCRIPTION OF THE INVENTION

Unless otherwise indicated, the term "$C_3$ to $C_{19}$" as employed herein alone or as part of another group includes both straight and branched chain hydrocarbons, containing 3 to 19 carbons, preferably 9 to 14 carbons, more preferably 11 to 13 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, tridecyl, quatradecyl, pentadecyl, hexadecyl, septadecyl, octadecyl, nonadecyl and the various branched chain isomers thereof, and the like, as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, adamantyl,

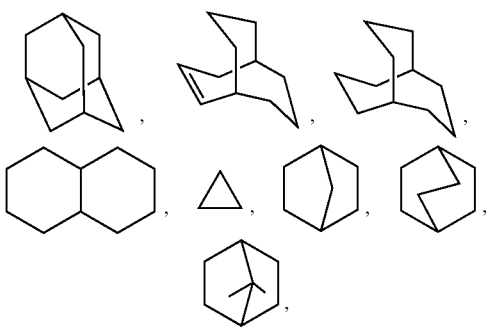

any of which groups may be optionally substituted with 1 to 4 substituents such as halogen, alkyl, alkoxy, hydroxy, aryl, aryloxy, arylalkyl, cycloalkyl, hydroxyalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

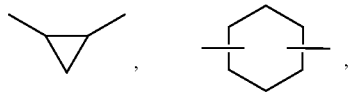

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatri-enyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as CF3, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

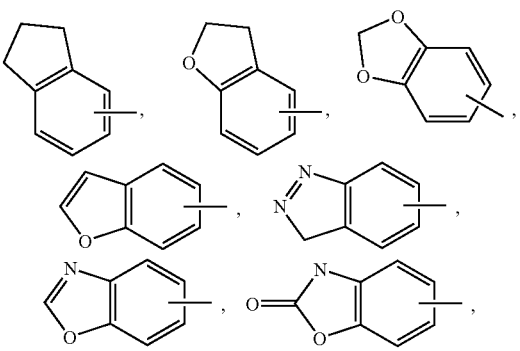

-continued

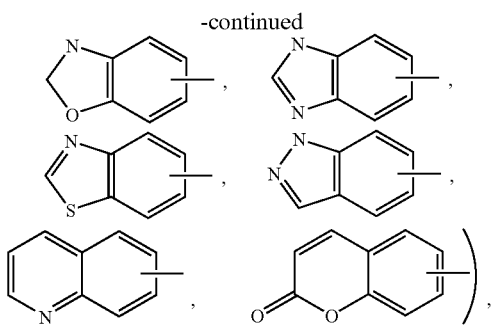

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

The $C_3$-$C_{19}$ alkyl thiotrifluoroacetate will preferably be $C_9$ to $C_{14}$-alkyl thiotrifluoroacetate and most preferably will be 1-dodecane thiotrifluoroacetate.

In carrying out the process of the invention for preparing the $C_3$ to $C_{19}$ alkyl- and aryl-thiotrifluoroacetates, the trifluoroacylating agent, which preferably is trifluoroacetic anhydride (TFAA), may also include (1-(trifluoroacetyl)imidazole, 3-(trifluoroacetyl)imidazole, trifluoroacetyl chloride, methyl trifluoroacetate, ethyl trifluoroacetate, propyl trifluoroacetate, isopropyl trifluoroacetate, butyl trifluoroacetate, vinyl trifluoroacetate, bismuth (III) triflate (Bi(OTF$_3$)) or 2-(trifluoroacetoxy)pyridine. The trifluoroacylating agent will be employed in a molar ratio to the $C_3$ to $C_{19}$ alkylthiol or arylthiol, which preferably is 1-dodecanethiol, within the range from about 1:1 to about 200:1, preferably from about 1:1 to about 2:1, more preferably from about 1:1 to about 1.1:1.

The organic base, which preferably is pyridine, may also be triethylamine, diethylamine, diisopropylamine, dimethylamine, tert-butylamine, diisobutylamine, N,N-diisopropylethyl amine (Hunig's base), 1,8-diazabicyclo{5.4.0}undec-7-ene (DBU), 1,5-diazabicyclo{4.3.0}non-5-ene (DBN), or 1,4-diazabicyclo{2.2.2}octane (DABCO). The organic base will be employed in a molar ratio to the $C_3$ to $C_{19}$ alkylthiol or arylthiol within the range from about 1:1 to about 200:1, preferably from about 1:1 to about 2:1, more preferably from about 1:1 to about 1.1:1.

The solvent which may be DCM, toluene, chloroform, THF, acetonitrile, methylacetate, ethyl acetate, isopropyl acetate, propyl acetate, butyl acetate, acetone, methylisobutyl ketone, methyl ethyl ketone, 1,2-dimethoxy ethane, 2-methyl tetrahydrofuran, 1,4-dioxane, methyl t-butyl ether, chlorobenzene, xylenes, heptane, hexanes, and cyclohexane, preferably is DCM.

The catalyst, which is preferably DMAP, will be employed in a molar ratio to the $C_3$ to $C_{19}$ alkylthiol or arylthiol within the range from about 0.0001:1 to about 200:1, preferably from about 0.001:1 to about 1:1.

The reaction of the $C_3$ to $C_{19}$ alkylthiol or the arylthiol and the trifluoroacylating agent will be carried out initially at a temperature within the range from about −50 to about 200° C., preferably from about 20 to about 40° C., and more preferably from about 0 to about 5° C. After addition of all components of the reaction, the reaction mixture will preferably be warmed, for example, to a temperature within the range from about −50 to about 200° C., preferably from about 20 to about 25° C.

In carrying out the process of the invention for protecting a primary or secondary amine, amino acid, amino alcohol or primary or secondary alcohol with the $C_3$ to the $C_{19}$ alkyl- or aryl-thiotrifluoroacetate protecting agent, the protecting agent will be employed in a molar ratio to the amine to be protected within the range form about 1:1 to about 1000:1, preferably from about 1:1 to about 5:1.

The reaction medium will be adjusted to a pH within the range from about 0 to about 14, preferably from about 8 to about 9.5, most preferably about 8.5 to about 9, employing aqueous base such as aqueous alkali metal hydroxide, preferably sodium hydroxide or potassium hydroxide.

The reaction is carried out at a temperature within the range from about −50 to about 200° C., preferably from about 50 to 65° C., more preferably from about 55 to about 60° C.

The process for protecting an amine, amino acid, amino alcohol or alcohol will be carried out employing an organic solvent such as THF, DMF, acetonitrile, methyl acetate, ethyl acetate, isopropyl acetate, propyl acetate, butyl acetate, acetone, methylisobutyl ketone, methyl ethyl ketone, 1,2-dimethoxy ethane, 2-methyl tetrahydrofuran, 1,4-dioxane, methyl t-butyl ether, chlorobenzene, xylenes, heptane, hexanes, cyclohexane, dimethyl sulfoxide, N-methyl pyrrolidine, methanol, ethanol, isopropanol, n-propanol, n-butanol, t-butanol, preferably THF or acetonitrile.

Examples of primary or secondary amine compounds, amino acids and primary and secondary alcohols, and amino alcohols which may be protected by the $C_3$-$C_{19}$ alkyl- and aryl-thiotrifluoroacetate of the invention include, but are not limited to

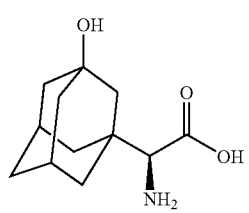

II all amino acids (RNH$_2$COOH where R is alkyl, aryl or cycloalkyl), primary and secondary alcohols such as R—OH or RCHOH where R is as deemed above, and amino alcohols such as serine or threonine.

Compound III may be employed in forming the anti-diabetic agent-antiobesity agent employing the following reaction sequence.

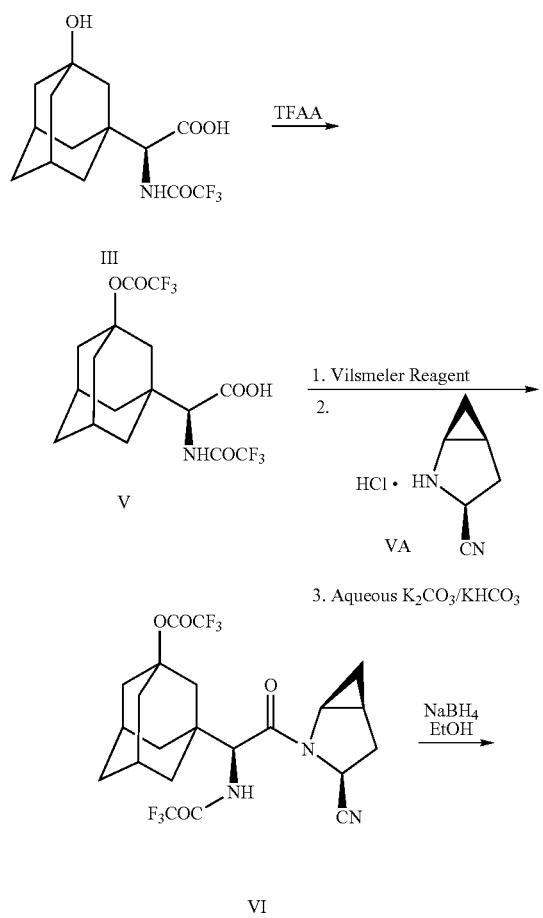

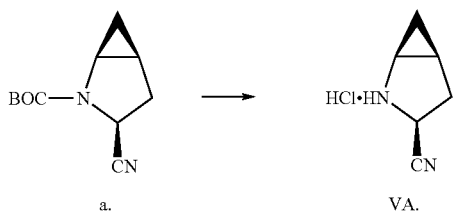

Compound VA may be prepared following the reaction scheme set out below

Compound a. is known in the literature, Registry No. 361442-57-1, U.S. Pat. No. 6,395,767, U.S. 2000-188555.20000310.

Compound VA is prepared by treating compound a. with HCl (gas) in ethyl acetate.

The following Examples represent preferred embodiments of the invention.

EXAMPLE 1

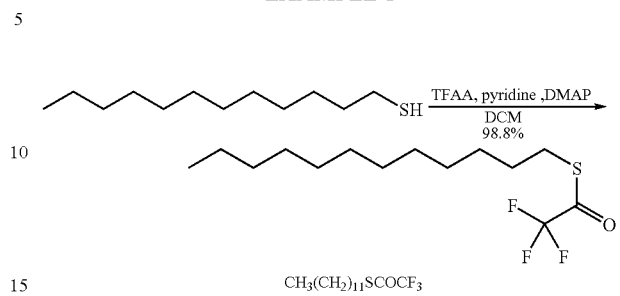

$CH_3(CH_2)_{11}SCOCF_3$

1-Dodecanethiol (75 mL, 312.7 mmol, 1.0 equiv) was added to a dry 2 L flask equipped with an overhead stirrer, temperature probe, condensor, and $N_2$ inlet/outlet. DCM (950 ml) was added. Pyridine (25.4 mL, 314 mmol, 1.0 equiv) was added followed by 42 mg of DMAP (0.344 mmol, 0.0011 equiv). The mixture was cooled to 0-5° C. TFAA (50.0 mL, 354 mmol, 1.13 equiv) was then added as a solution in 315 mL DCM. The addition was done at a rate slow enough to keep the reaction temperature at 0-5° C. The mixture was then warmed to 20-25° C. and stirred there for 1 h. Then the mixture was heated to 40° C. and held there for 1 h. The mixture was cooled to 20-25° C. and transferred to a separatory funnel. The mixture was washed with 950 mL DI water. The aqueous phase was back-extracted with 2×600 mL DCM. The combined organic phases were then washed with 600 mL DI water. The organic solution was then dried over $MgSO_4$. The solvent was then removed under vacuum to give 92.2 g of title compound as a clear liquid (98.8% yield). The title compound was found to be substantially odorless.

EXAMPLE 2

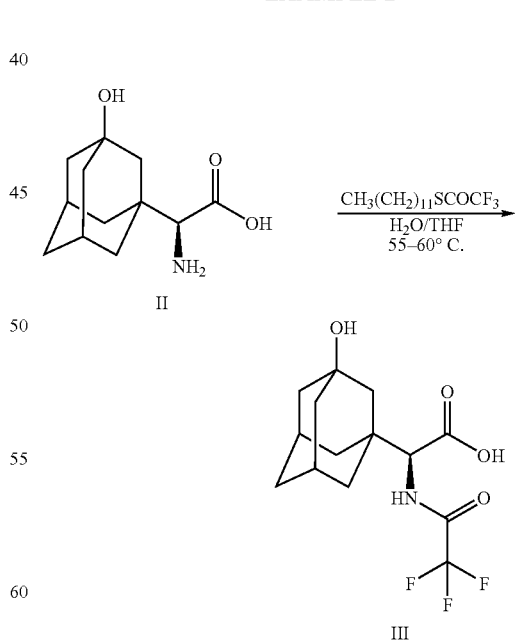

Trifluoroacetylation using $CH_3(CH_2)_{11}SCOCF_3$

A bioconversion mixture (20 mL) containing 2.0 g of compound II (prepared as described in U.S. Pat. No. 6,395,767)

(1.0 equiv, 8.87 mmole) was adjusted to pH 9.0 using 10 N NaOH. THF (20 mL) was added to the reaction mixture. 1-Dodecanethiotrifluoroacetate ($CH_3(CH_2)_{11}SCOCF_3$) (13.2 g, 5.0 equiv, 44.35 mmol) from Example 1 was then added and the mixture was heated to 55-60° C. The mixture was stirred at 55-60° C. for 5.5 h. During this time the pH was maintained at 8.5-9.0 using 10 N NaOH. A total of 4.0 mL of 10 N NaOH was used. The reaction was monitored by $^1$H NMR (see method below). After 5.5 h, the reaction mixture was cooled to 20-25° C. The THF was then removed under vacuum. EtOAc (35 mL) was added and the pH of the mixture was adjusted to 2.0 using 35% $H_2SO_4$. Celite (1 g) was added. The mixture was then filtered through a 1-g pad of celite. The celite cake was washed with 20 mL EtOAc. The pH of the filtrate was then adjusted back to 8.0 using 10 N NaOH. The phases were then separated. EtOAc (30 mL) was added to the aqueous phase and the pH was again adjusted to 2.0 using 35% $H_2SO_4$. The phases were separated. The EtOAc phase was concentrated to a total volume of approx. 7 mL. Heptane (46 mL) was added slowly to crystallize the product. The slurry was allowed to stir at 20-25° C. for 16 h. The slurry was then filtered and the cake was washed with 10 mL of heptane. The product was then dried under vacuum at 50° C. 2.20 g of title compound III was obtained as a white to off-white solid (77.2% yield).

The by-product from the above reaction, namely, 1-dodecanethiol was found to have no odor. $^1$H NMR method: 10 µL of the reaction mixture was dissolved in 250 µL of $CD_3CN$ and 500 µL $D_2O$. The α-amino proton signal for starting compound II appears at 3.28 ppm. The α-amino proton signal for title compound II appears at 4.1 ppm.

It will be appreciated that any of the primary and secondary amines, amino acids, primary and secondary alcohols and amino alcohols disclosed herein may be subjected to trifluoroacetylaction using $CH_3(CH_2)_{11}SCOCF_3$ as described in Example 2 to form protected amines or protected alcohols in accordance with the present invention.

What is claimed is:

1. A process for protecting a primary or secondary amine or amino acid, or a primary or secondary alcohol or an amino alcohol with a trifluoroacetyl protecting group which comprises treating an amino acid or a primary or secondary amine or a primary or secondary alcohol or an amino alcohol which needs to be protected with a $C_3$ to $C_{19}$ alkyl- or aryl-thiotrifluoroacetate in basic aqueous solution to form the corresponding trifluoroacetamide.

2. The process as defined in claim 1 wherein the process is for protecting an amine.

3. The process as defined in claim 1 wherein the $C_3$ to $C_{19}$ alkyl thiotrifluoroacetate is 1-dodecane thiotrifluoroacetate.

4. The process as defined in claim 1 wherein the amine to be protected is

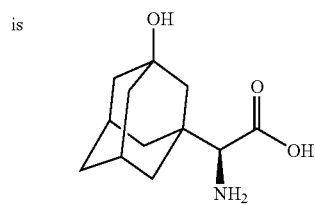

and the $C_3$-$C_{19}$ alkylthiotrifluoroacetate is 1-dodecane thiofluoroacetate and the protected amine formed is

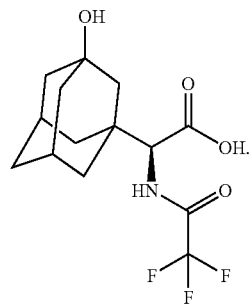

5. The process as defined in claim 1 wherein the amine to be protected is an amino acid of the structure $RCH(NH_2)COOH$ where R is alkyl, aryl or cycloalkyl.

6. The process as defined in claim 1 wherein the primary or secondary alcohol is R—OH or R—CHOH where R is alkyl, aryl or cycloalkyl.

7. The process as defined in claim 1 wherein the amino alcohol to be protected is serine or threonine.

8. The process as defined in claim 1 carried out in the presence of an organic solvent.

* * * * *

UNITED STATES PATENT AND TRADEMARK OFFICE
CERTIFICATE OF CORRECTION

| | |
|---|---|
| PATENT NO. | : 7,470,810 B2 |
| APPLICATION NO. | : 11/032734 |
| DATED | : December 30, 2008 |
| INVENTOR(S) | : Padam N. Sharma et al. |

It is certified that error appears in the above-identified patent and that said Letters Patent is hereby corrected as shown below:

Column 10, Lines 18-19 text is given as: "1-dodecane thiofluoroacetate".

Please replace with the following: "1-dodecane thiotrifluoroacetate".

Signed and Sealed this

Twenty-eighth Day of April, 2009

JOHN DOLL
*Acting Director of the United States Patent and Trademark Office*